US009632580B2

(12) United States Patent
Kim

(10) Patent No.: US 9,632,580 B2
(45) Date of Patent: Apr. 25, 2017

(54) ULTRASONIC APPARATUS AND METHOD OF CONTROLLING THE SAME

(71) Applicant: SAMSUNG ELECTRONICS CO., LTD., Suwon-si (KR)

(72) Inventor: Yun-tae Kim, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 17 days.

(21) Appl. No.: 14/796,002

(22) Filed: Jul. 10, 2015

(65) Prior Publication Data

US 2016/0034031 A1    Feb. 4, 2016

(30) Foreign Application Priority Data

Jul. 30, 2014    (KR) ........................ 10-2014-0097122

(51) Int. Cl.
  G06F 3/01    (2006.01)
  G06T 7/00    (2006.01)
  G06T 11/60   (2006.01)
  A61B 8/00    (2006.01)
  A61B 8/08    (2006.01)
  G01S 7/52    (2006.01)
  G01S 15/89   (2006.01)

(52) U.S. Cl.
  CPC ............. *G06F 3/013* (2013.01); *A61B 8/461* (2013.01); *A61B 8/466* (2013.01); *A61B 8/467* (2013.01); *A61B 8/5261* (2013.01); *G01S 7/52068* (2013.01); *G01S 7/52074* (2013.01); *G01S 7/52084* (2013.01); *G01S 15/899* (2013.01); *G06T 11/60* (2013.01); *A61B 8/4405* (2013.01)

(58) Field of Classification Search
  CPC ................ G09G 5/14; G09G 2340/10; G09G 2340/125; G06T 11/60; H04N 5/44504
  See application file for complete search history.

(56) References Cited

U.S. PATENT DOCUMENTS

| | | | | |
|---|---|---|---|---|
| 5,810,007 | A | * | 9/1998 | Holupka ................ A61B 8/08 600/407 |
| 2002/0128550 | A1 | * | 9/2002 | Van Den Brink ....... A61B 8/00 600/411 |
| 2008/0009719 | A1 | * | 1/2008 | Shuros ................ A61B 5/0031 600/427 |
| 2008/0071172 | A1 | * | 3/2008 | Bruck ................. A61B 5/0059 600/438 |
| 2010/0054630 | A1 | * | 3/2010 | Avinash ............. G06F 3/04845 382/294 |

(Continued)

*Primary Examiner* — Todd Buttram
(74) *Attorney, Agent, or Firm* — Sughrue Mion, PLLC

(57) ABSTRACT

Disclosed are an ultrasonic apparatus for displaying one of an ultrasonic image, an external image and a composite image thereof by recognizing the position of eyes of a user, and a control method thereof. The ultrasonic apparatus includes a storage configured to store an external image of an object, an image processor configured to generate a composite image by registering an ultrasonic image of the object with respect to the stored external image, a recognizer configured to recognize a position of eyes of a user, and a display configured to display one of the ultrasonic image, the external image and the composite image of the ultrasonic image and the external image, based on the recognized position of the eyes of the user.

20 Claims, 17 Drawing Sheets

(56) References Cited

U.S. PATENT DOCUMENTS

| | | | |
|---|---|---|---|
| 2010/0239144 A1* | 9/2010 | Fichtinger | A61B 5/418 382/131 |
| 2011/0046483 A1* | 2/2011 | Fuchs | A61B 8/00 600/439 |
| 2013/0307935 A1* | 11/2013 | Rappel | A61B 1/00048 348/46 |
| 2014/0327613 A1* | 11/2014 | Chessa | H04N 13/0014 345/156 |
| 2015/0011875 A1* | 1/2015 | Noordhoek | A61B 6/035 600/426 |
| 2015/0023589 A1* | 1/2015 | Kataoka | G06T 15/20 382/154 |
| 2015/0257735 A1* | 9/2015 | Ball | A61B 8/5261 600/440 |
| 2015/0297311 A1* | 10/2015 | Tesar | A61B 90/361 600/411 |
| 2015/0306423 A1* | 10/2015 | Bharat | A61N 5/1048 600/427 |
| 2016/0220324 A1* | 8/2016 | Tesar | G02B 21/0012 |

\* cited by examiner

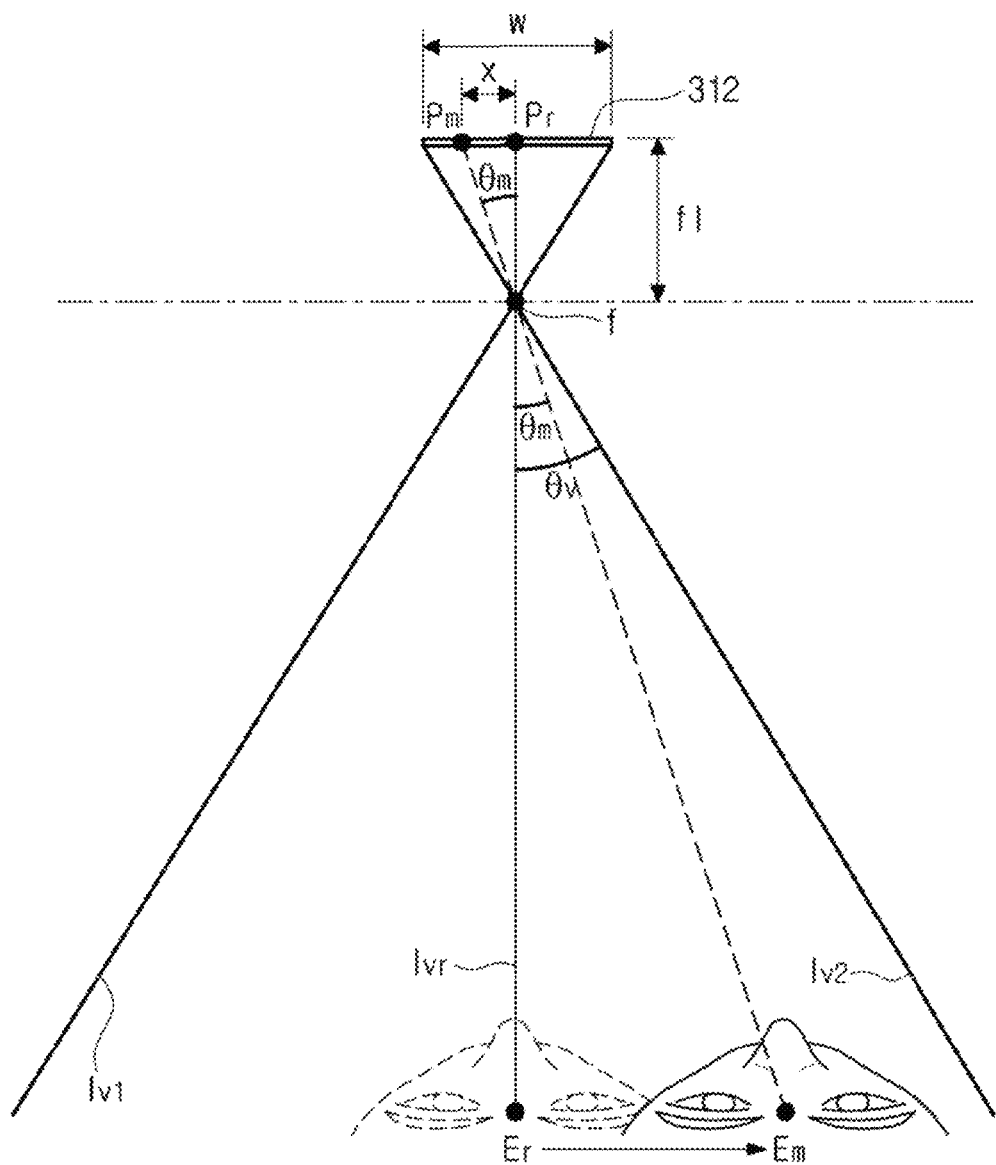

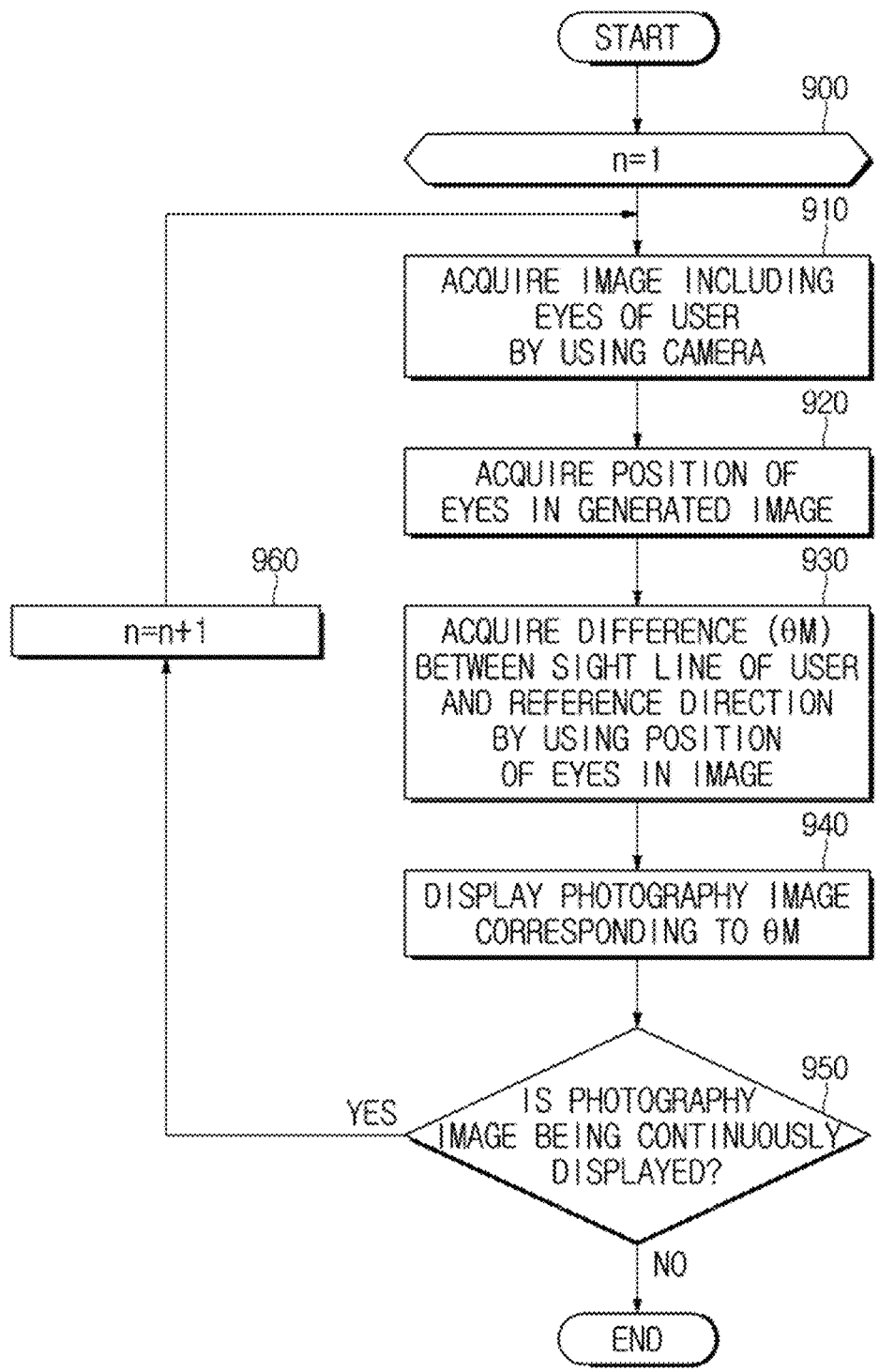

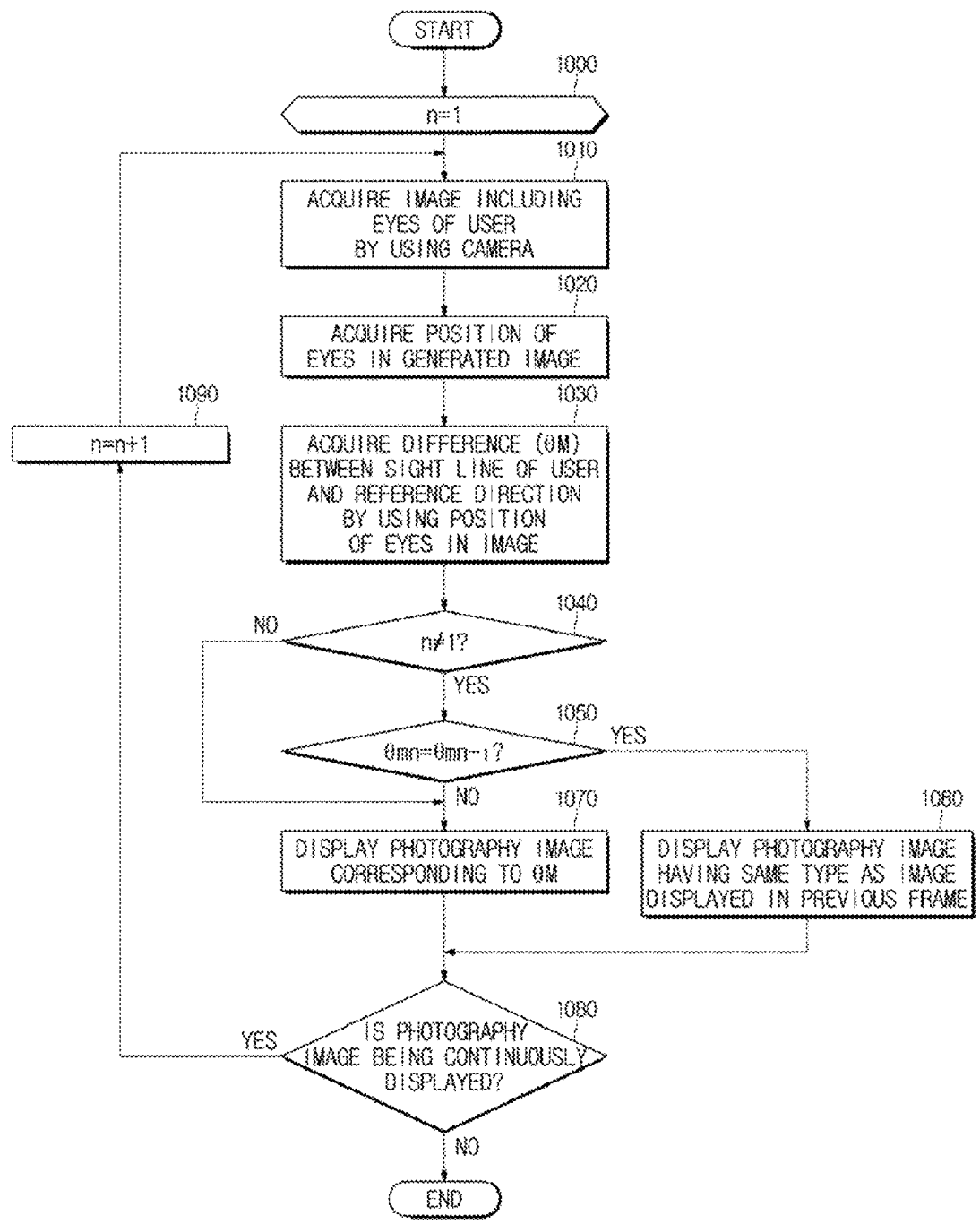

ULTRASONIC APPARATUS AND METHOD OF CONTROLLING THE SAME

CROSS-REFERENCE TO RELATED APPLICATIONS

This application claims priority from Korean Patent Application No. 10-2014-0097122, filed on Jul. 30, 2014 in the Korean Intellectual Property Office, the disclosure of which is incorporated herein by reference in its entirety.

BACKGROUND

1. Field

Exemplary embodiments relate to an ultrasonic apparatus for imaging an ultrasonic signal, and a method of controlling the same.

2. Description of the Related Art

An ultrasonic diagnosis apparatus operates to irradiate ultrasonic waves through the surface of an object toward an object portion within the object, and the apparatus receives an ultrasonic echo signal reflected from the object portion in order to obtain a cross-sectional image of a soft tissue or bloodstream in a non-invasive manner.

The ultrasonic diagnosis apparatuses are smaller in size and cheaper compared to other image diagnostic devices. Thus, these ultrasonic imaging apparatuses are widely used for heart diagnosis, abdominal diagnosis, urological diagnosis and obstetric and gynecological diagnosis.

In recent years, many studies have been conducted on an ultrasonic diagnosis apparatus for providing a user with a composite image obtained by combining an ultrasonic image with a computed tomography (CT) image or and a magnetic resonance (MR) image. Such an ultrasonic diagnosis apparatus is configured to simultaneously or selectively provide a user with an ultrasonic image, a CT image, an MR image or a composite image thereof.

SUMMARY

Therefore, it is an aspect of one or more exemplary embodiments to provide an ultrasonic apparatus capable of displaying one of an ultrasonic image, an external image and a composite image of the ultrasonic image and the external image by recognizing the position of eyes of a user, and a method of controlling the same.

Additional aspects of the exemplary embodiments will be set forth in part in the description which follows and, in part, will be obvious from the description, or may be learned by practice of the exemplary embodiments.

In accordance with one aspect, an ultrasonic apparatus includes a storage, an image processor, a recognizer, and a display. The storage may be configured to store an external image of an object. The image processor may be configured to generate a composite image by registering an ultrasonic image of the object with respect to the stored external image. The recognizer may be configured to recognize a position of eyes of a user. The display may be configured to display one of the ultrasonic image, the external image and the composite image of the ultrasonic image and the external image, based on the recognized position of the eyes of the user.

In accordance with one aspect of one or more exemplary embodiments, a method for controlling an ultrasonic apparatus includes: generating a composite image by registering an ultrasonic image of an object with respect to an external image of the object; recognizing a position of eyes of a user; and displaying one of the ultrasonic image, the external image and the composite image, based on the recognized position of the eyes of the user.

BRIEF DESCRIPTION OF THE DRAWINGS

These and/or other aspects will become apparent and more readily appreciated from the following description of exemplary embodiments, taken in conjunction with the accompanying drawings of which:

FIG. 4 is a view describing a method of recognizing the position of eyes of a user in a controller of an ultrasonic apparatus, in accordance with an exemplary embodiment;

FIG. 11 is a flowchart showing a method of controlling an ultrasonic apparatus, in accordance with still another exemplary embodiment; and FIG. 12 is a flowchart showing a method of controlling an ultrasonic apparatus, in accordance with still another exemplary embodiment.

DETAILED DESCRIPTION

Figure 1:
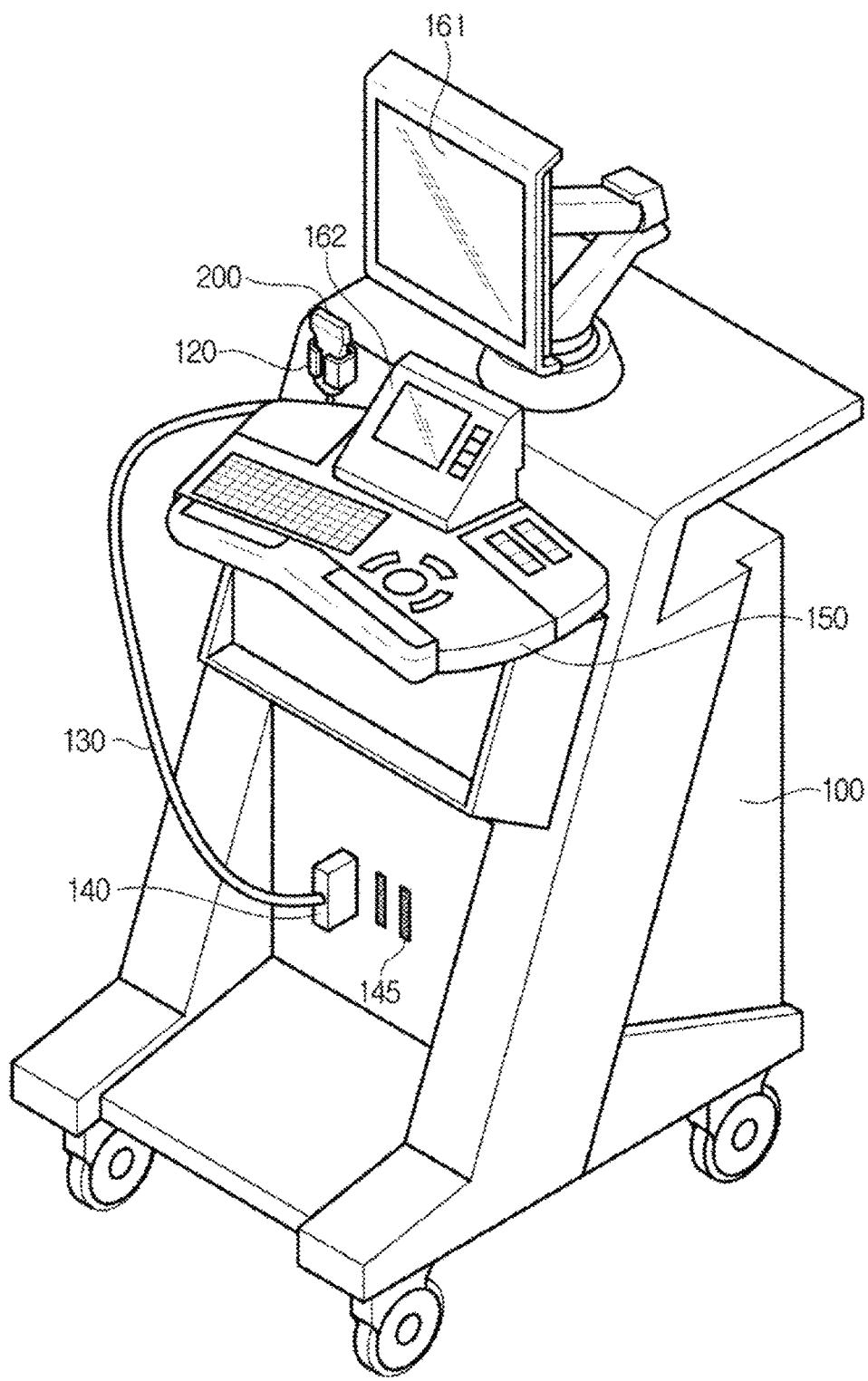
FIG. 1 is a perspective view illustrating an ultrasonic apparatus, in accordance with one exemplary embodiment.

Reference will now be made in detail to exemplary embodiments, examples of which are illustrated in the accompanying drawings, wherein like reference numerals refer to like elements throughout.

FIG. 1 is a perspective view illustrating an ultrasonic apparatus, in accordance with one exemplary embodiment. Referring to FIG. 1, an ultrasonic apparatus includes a main body 100, an ultrasonic probe 200, an input (also referred to herein as an "input unit") 150 and a display 160.

One or more female connectors 145 may be provided at one side of the main body 100. A male connector 140 connected to a cable 130 may be physically coupled to the female connector 145.

Meanwhile, a plurality of casters (not shown) may be provided at a lower portion of the main body 100 for mobility of the ultrasonic apparatus. The plurality of casters may be provided to enable the ultrasonic apparatus to be fixed to a certain location or to be moved in a particular direction. Such an ultrasonic apparatus may be referred to as a cart type ultrasonic apparatus.

Alternatively, different from FIG. 1, the ultrasonic apparatus may be provided as a portable ultrasonic apparatus that may be portable while in a remote movement. In this case, the portable ultrasonic apparatus may be not provided with a caster. Examples of the portable ultrasonic apparatus may include PACS Viewer, smart phone, lap top computer, PDA, and table PC, but the portable ultrasonic apparatus is not limited thereto.

The ultrasonic probe 200 is a portion which makes contact with a body surface of an object, and may be configured to transmit and receive an ultrasonic wave. Specifically, the ultrasonic probe 200, according to a transmission signal which is provided from the main body 100, transmits an ultrasonic signal to the inside of the object, receives an ultrasonic echo signal reflected from a specific portion inside the object, and transmits the received ultrasonic echo signal to the main body 100.

The cable 130 may have one end connected to the ultrasonic probe 200 and the other end connected to the male connector 140. The male connector 140 connected to the other end of the cable 130 may be physically coupled to the female connector 145 of the main body 100.

Alternatively, different from FIG. 1, the ultrasonic probe 200 may be connected to the main body in a wireless scheme. In this case, the ultrasonic probe 200 may transmit the ultrasonic echo signal, which is received from the object, to the main body. In addition, a single main body may be connected to a plurality of ultrasonic probes 200.

The ultrasonic probe 200 may be classified based on an arrangement of transducer elements 210.

Figure 2A:
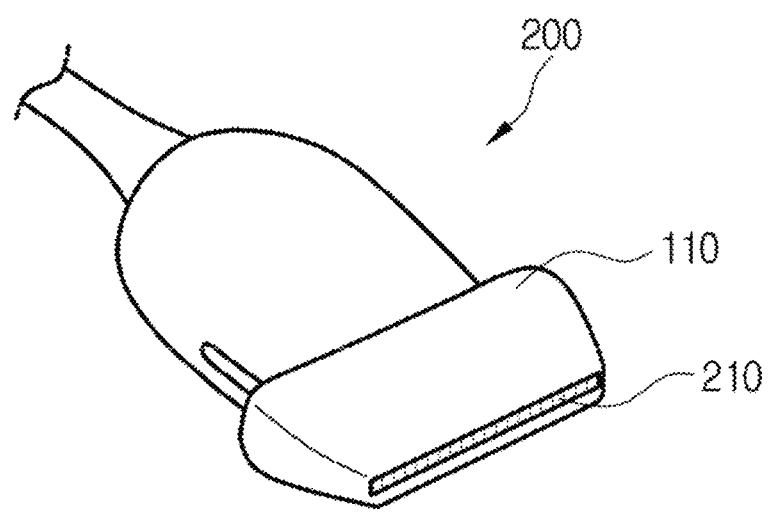
FIGS. 2A and 2B are perspective views illustrating ultrasonic probes depending on arrangement of transducer elements, in accordance with various exemplary embodiments.
Figure 2B:
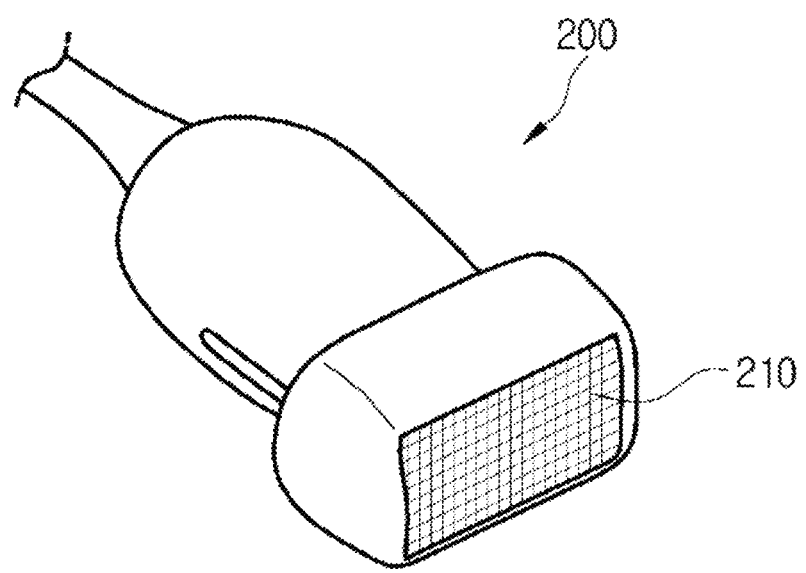

FIGS. 2A and 2B are perspective views illustrating ultrasonic probes depending on arrangement of transducer elements, in accordance with various exemplary embodiments. FIG. 2A is a view illustrating a one-dimensional array probe, and FIG. 2B is a view illustrating a two-dimensional array probe.

The type of the ultrasonic probe 200 may be classified in accordance with the arrangement of transducer elements 210. Referring to FIG. 2A, the ultrasonic probe 200 having transducer elements 210 arranged on one surface thereof in a 1D manner is referred to as an one-dimensional (1D) array probe. The one-dimensional (1D) array probe includes a linear array probe in which the transducer elements 210 are arranged in a straight line, a phased array probe, and a convex array probe in which the transducer elements 210 are arranged in a curved line. Unlike this, the ultrasonic probe 200 having the transducer elements 210 arranged in a 2D manner is referred to as a 2D array probe. As shown in FIG. 2B, the transducer elements 210 may be arranged on one surface of the 2D array probe 200 while forming a flat surface. Alternatively, the transducer elements 210 may be arranged on one surface of the 2D array probe 200 while forming a curved surface.

Referring again to FIG. 1, the main body may include an image processor 170 configured to convert an ultrasonic echo signal received by the ultrasonic probe 200 into an ultrasonic image. The image processor 170 may be implemented as hardware, such as a microprocessor, or may be implemented as software executed on hardware.

The image processor 170 may generate an ultrasonic image by performing a scan conversion on the ultrasonic echo signal. The ultrasonic image may include not only a gray scale image obtained by scanning an object in an amplitude mode (A-mode), a brightness mode (B-mode), or a motion mode (M-mode), but also a Doppler image that represents a moving object by using a Doppler effect. The Doppler image includes a tissue Doppler image which represents movement of tissues and a spectral Doppler image which represents the moving speed of an object as a waveform.

The image processor 170, in order to generate a B-mode image, may extract a B-mode component from the ultrasonic echo signal received by the ultrasonic probe 200. The image processor 170 may generate an ultrasonic image that represents the intensity of an ultrasonic echo signal as a brightness, based on the B-mode component.

Similarly, the image processor 170 may extract a Doppler component from the ultrasonic echo signal, and generate a Doppler image that represents the movement of an object as a color or waveform, based on the extracted Doppler component.

In addition, the image processor 170, by performing a volume rendering on the volume data acquired via the ultrasonic echo signal, may generate a 3D ultrasonic image, and also generate an elasticity image which shows a degree to which an object is deformed by pressure. In addition, the image processor may represent various types of additional information on the ultrasonic image in the form of texts and graphics.

Meanwhile, the generated ultrasonic image may be stored inside the main body or in a storage 400 outside the main body. Alternatively, the ultrasonic image may be storage in a web storage configured to perform a storage function on the web, or in a cloud server.

The input unit 150 is configured to receive a command associated with an operation of the ultrasonic apparatus. For example, the input unit 150 may receive a command for selecting a mode(s) such as an A-mode, a B-mode, and/or a M-mode or a Doppler image mode. In addition, the input unit 150 may receive a start command for an ultrasonic diagnosis.

The command received via the input unit 150 may be transmitted to the main body 100 over wired or wireless communication.

The input unit 150 may include, for example, at least one of a keyboard, a foot switch, and a foot pedal. The keyboard may be implemented as hardware and positioned on an upper portion of the main body 100. The keyboard may include at least one of a switch, a key, a joystick, and a tack ball. Alternatively, the keyboard may be implemented as software such as a graphical user interface. In this regard, the keyboard may be displayed on a main display 161 or a sub display 162. The foot switch or foot pedal may be disposed at a lower portion of the main body 100. The user may control an operation of the ultrasonic apparatus by using the foot pedal.

The display 160 may include the main display 161 and the sub display 162.

The sub display 162 may be disposed at the main body 100. FIG. 1 illustrates that the sub display 162 is disposed on the input unit 150. The sub display 162 may display an application associated with an operation of the ultrasonic apparatus. For example, the sub display 162 may display a menu or instruction required for an ultrasonic diagnosis. The sub display 162 may include any of a cathode ray tube (CRT), a liquid crystal display (LCD), and/or the like.

The main display 161 may be disposed at the main body 100. In FIG. 1, the main display 161 is disposed over the sub display 162. The main display 161 may display an ultrasonic image acquired during the ultrasonic diagnosis, according to an input applied to the input unit 150. The main display 161 may include any of a CRT, an LCD, and/or the like in the same manner as the sub display 162. FIG. 1 illustrates that the main display 161 is coupled to the main body 100. However, the main display 161 may be detachably disposed on the main body 100.

In FIG. 1, the ultrasonic apparatus is provided with both the main display 161 and the sub display 162. However, the sub display 162 may be omitted if necessary. In this case, the application or menu displayed on the sub display 162 may be displayed on the main display 161.

The display 160 may be designed such that a three dimensional image is provided to a user. In detail, the display 160 may be designed such that the left eye and the right eye of a user recognize different images, respectively, and thus receive a three dimensional image based on a binocular parallax.

The display 160 may adopt a stereoscopic method or an autostereoscopic method such that a user recognizes a three dimensional image.

The stereoscopic method may be achieved by using glasses, for example, polarizer glasses or LC shutter glasses, configured to represent a three dimensional image. The autostereoscopic method may be achieved by using devices, such as a lenticular lens, a parallax barrier, and a parallax illumination, such that a three dimensional image is viewed with the naked eye.

In addition, the display 160 may further include a camera configured to a capture a sightline of a user. Details thereof will be described below.

Meanwhile, the ultrasonic apparatus may further include a communication unit (also referred to herein as a "communicator" and/or as a "transceiver"). The communication unit is connected to a network 500 in a wired or wireless scheme, to communicate with an external apparatus or an external server. The communication unit may exchange data with a hospital server connected via a Picture Archiving and Communication System (PACS) or other medical devices in a hospital. In addition, the communication unit may perform a data communication according to standards for Digital Imaging and Communications in Medicine (DICOM).

The communication unit may transmit and receive object diagnosis-related data, such as ultrasonic images, ultrasonic echo signals, and Doppler data of an object, through the network 500, and may transmit and receive a medical image photographed by another medical device, for example, CT, MRI and X-ray images. In addition, the communication unit may receive information which relates to a diagnosis history of a patient or a treatment plan from the server, and use the received information for diagnosis. In addition, the communication unit may perform a data communication with a portable terminal of a doctor or a patient.

The communication unit is connected to the network 500 in a wired or wireless scheme, to exchange data with a server, a medical device or a portable terminal. The communication unit may include one or more elements that facilitate communication with an external device, for example, a near field communication module, a wired communication module and a mobile communication module.

The near field communication module represents a module configured to perform a near field communication within a predetermined range. Examples of the near field communication technology according to an exemplary embodiment may include any of Wireless LAN, Wi-Fi, Bluetooth, Zigbee, Wi-Fi Direct (WFD), Ultra wideband (UWB), Infrared Data Association (IrDA), Bluetooth Low Energy (BLE), and Near Field Communication (NFC), but is not limited thereto.

The wired communication module represents a module configured to perform a communication by using an electric signal or an optical signal. Examples of the wired communication technology according to an exemplary embodiment may include any of a pair cable, a coaxial cable, an optical fiber cable and an Ethernet cable.

The mobile communication module is configured to transmit and/or receive a wireless signal with at least one of a base station, an external terminal and an external server. The wireless signal may include any of an audio call signal, a video call signal, or various type of data according to transmission and reception of text/multimedia messages.

Figure 3A:
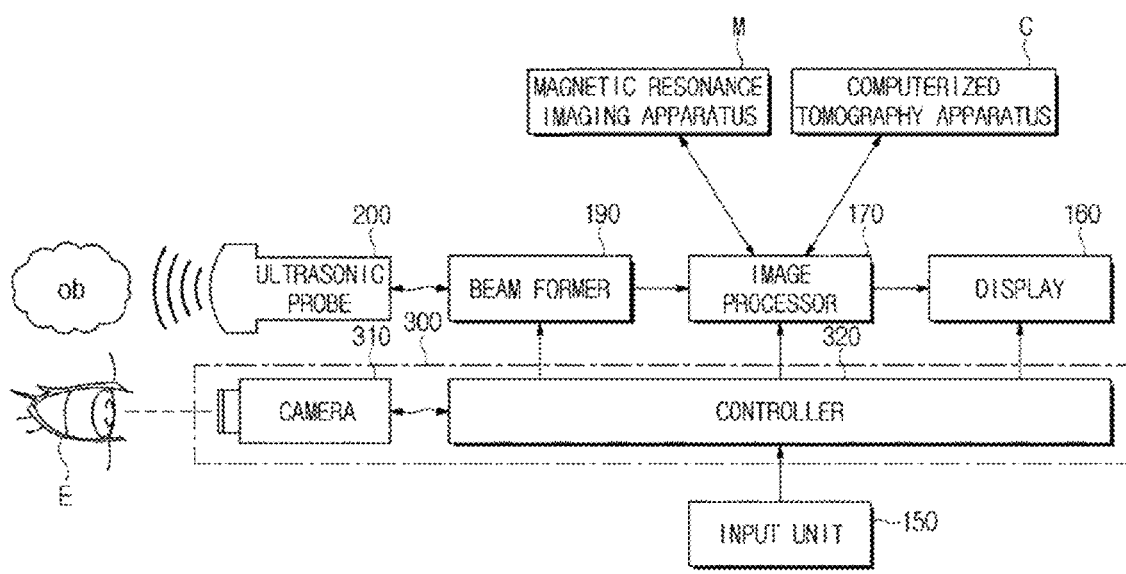
FIGS. 3A, 3B, and 3C are block diagrams illustrating ultrasonic apparatuses, in accordance with various exemplary embodiments.
Figure 3B:
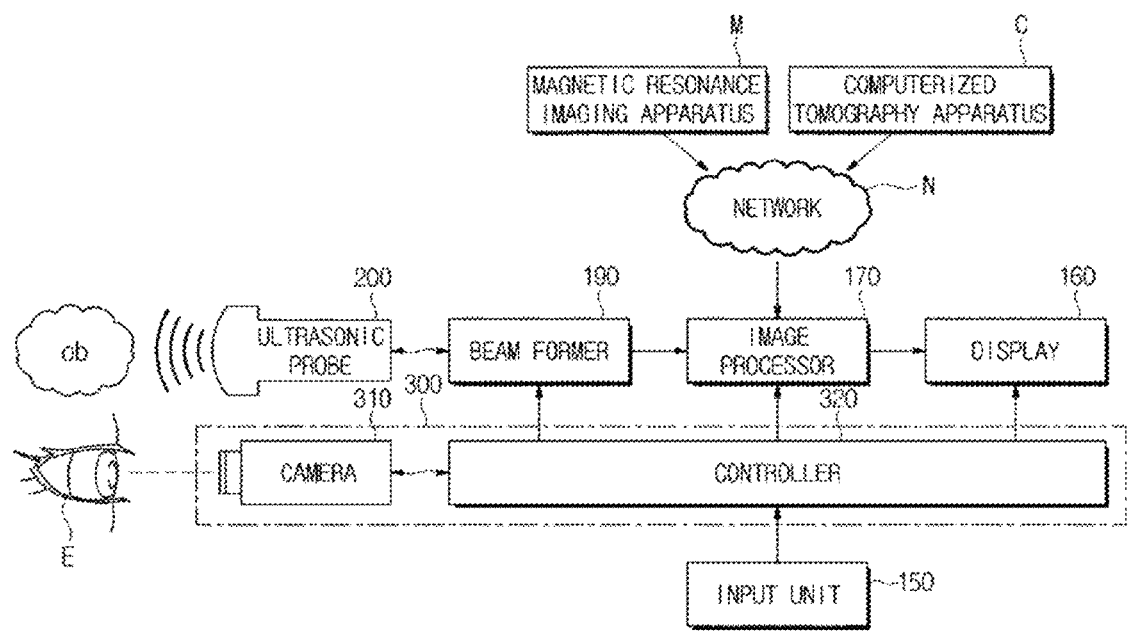
Figure 3C:
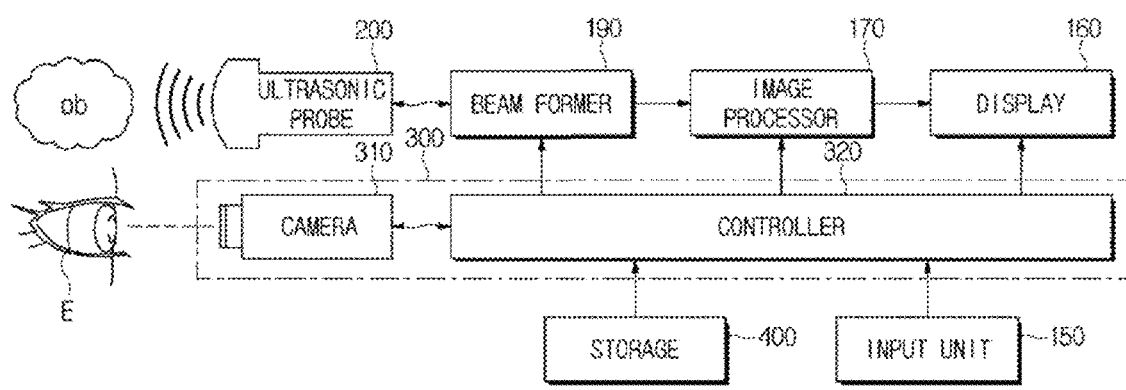

FIGS. 3A, 3B, and 3C are block diagrams illustrating ultrasonic apparatuses, in accordance with various exemplary embodiments.

Referring to FIG. 3A, the ultrasonic apparatus includes the ultrasonic probe 200 configured to irradiate ultrasonic waves toward an object ob, and to receive the ultrasonic echo waves reflected from the object ob, a beamformer 190 configured to collect ultrasonic waves or echo ultrasonic waves, the image processor 170 configured to generate an ultrasonic image based on the collected echo ultrasonic waves; and the display 160 configured to display the generated ultrasonic image.

In addition, the ultrasonic apparatus may further include a recognizer 300 configured to recognize the position of eyes of a user. In detail, the recognizer 300 may include a camera 310 configured to acquire an image which includes the eyes of a user; and a controller 320 configured to determine the position of the eyes of a user, based on the position of the eyes in the acquired image. Hereinafter, parts identical to those of the above description of FIG. 1 will be omitted, and the following description will be made in relation to an ultrasonic apparatus according to an exemplary embodiment that is configured to display a different image according to the sightline of a user.

As described above, the ultrasonic probe 20 may acquire echo ultrasonic waves which include internal data which relates to an object ob. The internal data which relates to an object may include data which relates to a cross section of the object ob, and volume data which includes a plurality of pieces of cross section data.

In particular, in order to acquire the volume data about an object ob, a 1D array probe may acquire a plurality of pieces of plane data via a user's manipulation, or acquire a plurality of pieces of plane data via mechanical movement.

Different from the 1D array probe, the 2D array probe may acquire volume data about an object ob by irradiating and steering ultrasonic waves. In this case, it is possible to acquire a volume data by irradiating ultrasonic waves in the form of a plane wave.

If the ultrasonic probe 200 receives echo ultrasonic waves, the beamformer 190 may collect the received echo ultrasonic waves. The beamformer 190 may perform beamforming by adopting any one of generally known beamforming methods.

The image processor 170 may generate ultrasonic images based on the collected echo ultrasonic waves. In addition, the image processor 170 may receive an external image of an object ob from an external apparatus, and may combine the external image with the ultrasonic image by registering the external image with respect to the ultrasonic image.

The external apparatus represents an apparatus configured to generate a photography image by photographing an object ob, and the external apparatus may include a magnetic resonance imaging apparatus M and a computerized tomography apparatus C. In addition, the external image is a photography image generated by the external apparatus, and may include an MR image generated by the magnetic resonance imaging apparatus M and a CT image generated by the computerized tomography apparatus C.

Referring to FIG. 3A, the image processor 170 may directly receive an MR image or a CT image by being directly connected to the magnetic resonance imaging apparatus M and the computerized tomography apparatus C. Although not shown in FIG. 3A, the image processor 170 may directly receive a PET image from a positron emission tomography (PET) apparatus, or may directly receive an X-ray image from an X-ray imaging apparatus.

The image processor 170 may register the generated ultrasonic image to an external image received from the external apparatus. The registering represents aligning coordinate systems of the ultrasonic image and the external image. As a result, a user may be supplied with different photography images with respect to the same object ob, which enhances the precision of diagnosis.

In addition, the image processor 170 may generate a composite image by combining the ultrasonic image and the external image that have been registered with respect to each other. The image compositing represents overlaying different images, based on the coordinate systems that are aligned according to the registration.

In this case, the composition ratio of the compositing image is determined by ratios of opacity of overlaid images. For example, a composite image which includes 80% of an ultrasonic image and 20% of a CT image represents an image obtained by overlaying an ultrasonic image having an opacity of 80% with a CT image having an opacity of 20%.

Meanwhile, the camera 310 may acquire an image which includes eyes E of a user. In this case, the camera 310 may acquire an image which includes the eyes of a user in real time. The acquiring of an image in real time represents capturing a region which includes the eyes of a user according to a predetermined frame rate.

To this end, the camera 310 may include a lens configured to form a focal point by collecting light; and an image pickup device configured to form an image from light passing through the lens.

The image pickup device captures an image of eyes E by forming an optical image with respect to eyes E of a user on an image plane.

The controller 320 may determine the actual position of the eyes E of a user based on the position of the eyes in the image acquired by the camera 310. The position of the eyes of a user in an image may represent the position of an optical image of eyes that are imaged on the image plane. In addition, the actual position of the eyes E of a user may represent the position of the eyes of a user in a space in which the user exists. The following description will be made with reference to FIG. 4 in relation to the controller 320 determining the position of the eyes of a user.

FIG. 4 is a view describing a method for recognizing position of eyes of a user in the controller of the ultrasonic apparatus, in accordance with an exemplary embodiment, in which $I_{vr}$ represents an optical axis of the lens, a region between $I_{v1}$ and $I_{v2}$ is a region possible to be captured by the camera 310, and an angle between $I_{v1}$ and $I_{v2}$ represents an angle of view of the camera 310. In addition, the description of FIG. 4 will be made on the assumption that the position of the eyes E is the middle of a left eye and a right eye.

When the position of the eyes E of a user is changed from a reference position $E_r$ to the current position $E_m$, an optical image of the eyes is formed on an image plane $P_m$ of the image pickup device. When a point $P_r$ passed by an optical axis on the image plane is the origin of a reference coordinate, a difference X between $P_r$ and Pm corresponds to the position of the eyes.

In this case, the difference X may be obtained by using the number of pixels on the image plane.

After the position X of the eyes in the acquired image is determined, the controller 320 may determine the actual position of the eyes of the user. In detail, the controller 320 may acquire an angle $\theta_m$ formed between a sightline of the user (i.e., a direction starting the position of eyes of the user and oriented at the center of the lens of the camera 310) and a reference line (i.e., an optical axis).

In this case, the controller 320 may acquire $\theta_m$ according to Equation 1 below.

$$\theta_m = \tan^{-1}\left(\frac{x}{fl}\right) \qquad \text{[Equation 1]}$$

$\theta_m$ represents an angle between a sightline of a user and the reference line, and X represents the position of the eyes in the acquired image, and fl represents a focal distance of the camera 310.

Meanwhile, the focal distance fl of the camera 310 may be determined according to Equation 2 below.

$$fl = \frac{w/2}{\tan(\theta_v)} \qquad \text{[Equation 2]}$$

fl represents the focal distance of the camera 310, w represents the width of the image plane, and $\theta_v$ represents ½ of the angle of view of the camera 310.

Although the method for determining the position of eyes of a user according to an exemplary embodiment is implemented by using Equation 1 and Equation 2, the exemplary embodiments are not limited thereto. Accordingly, the controller 320 may apply various types of Eye-tracking methods within the technical field of the exemplary embodiments with respect to determining the actual position of eyes E based on the position of the eyes E in an image which includes the eyes E of a user.

According to Equation 1 and Equation 2, the angle $\theta_m$ formed between the sightline of the user and the reference line is acquired, and the controller 320 may control the display 160 to display an image having a type corresponding to $\theta_m$.

Figure 5A:
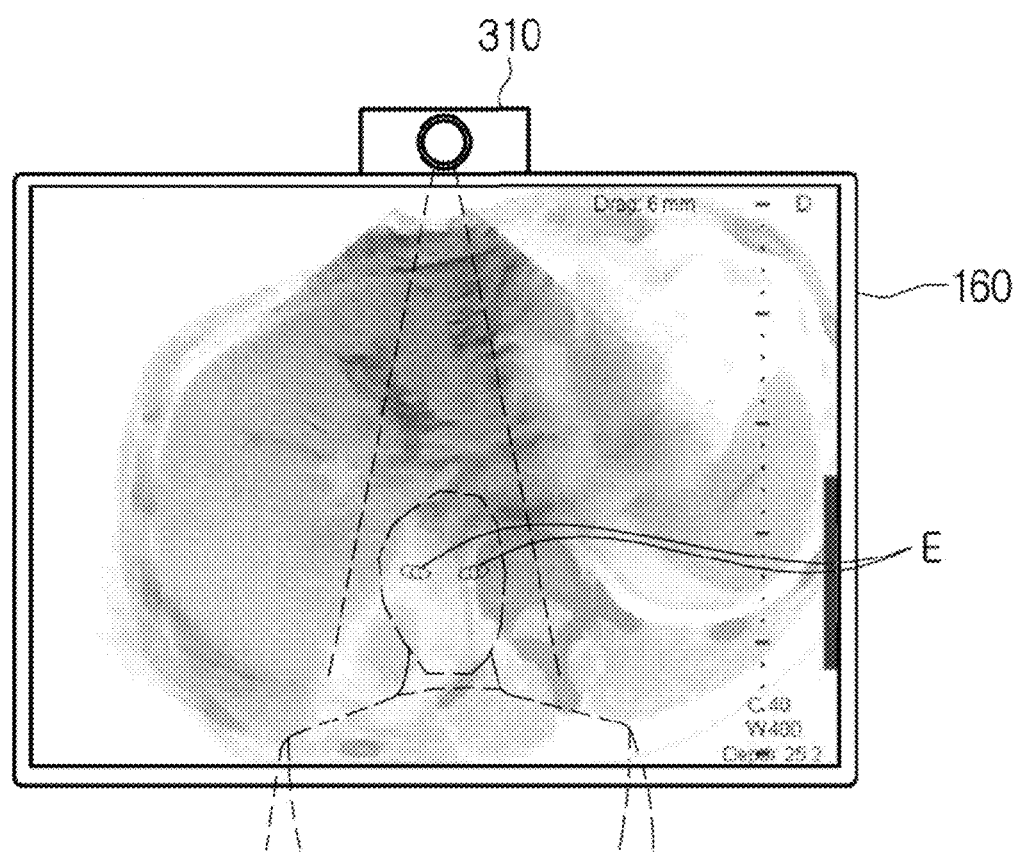
FIGS. 5A, 5B, and 5C are views illustrating a display method of an ultrasonic apparatus, in accordance with an exemplary embodiment.
Figure 5B:
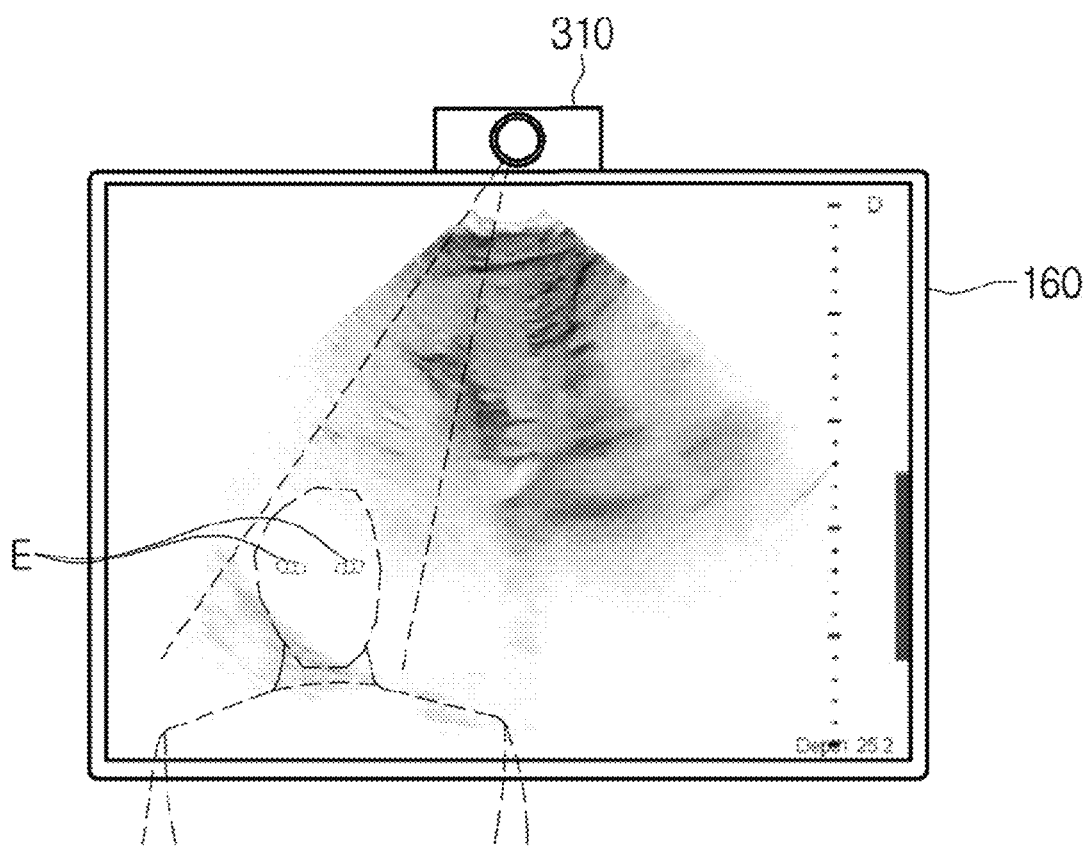
Figure 5C:
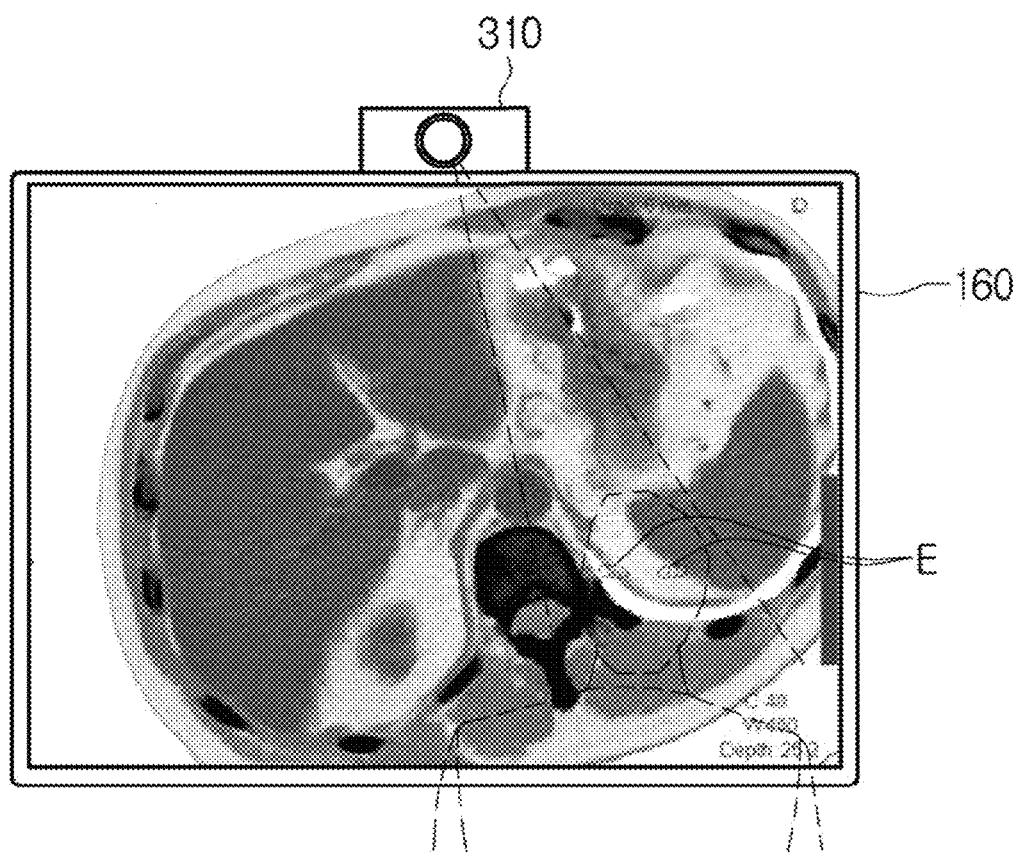

FIGS. 5A, 5B, and 5C are views illustrating a display method in the display 160, in accordance with an exemplary embodiment.

The controller 320 controls the display 160 to display a composite image of an object ob if the recognized position of eyes E belongs to a predetermined first region, to display an ultrasonic image of an object ob if the recognized position of the eyes E belongs to a predetermined second region, and to display an external image of an object ob if the recognized position of the eyes belongs to a predetermined third region. The description of FIGS. 5A, 5B, and 5C will be made on the assumption that the external image is a CT image.

FIG. 5A illustrates that eyes E of a user are positioned in the first region. In FIG. 5A, the first region may represent a region between dotted lines extending from the camera 310.

If the camera 310 acquires an image which includes eyes E of a user, the controller 320 may determine the position of the eyes E of the user based on the acquired image. If the position of the eyes E of the user is provided in the first region, the controller 320 may control the display 160 to display a composite image of an object ob. In this case, the composite image is an image obtained by combining an ultrasonic image of an object ob with a CT image of the object ob.

FIG. 5B illustrates that eyes E of a user are positioned in the second region. In FIG. 5B, the second region may represent a region between dotted lines extending from the camera 310.

The controller 320 may determine the actual position of eyes E of the user based on the position of the eyes of a user in the acquired image. If the determined position of the eyes E of the user is provided in the second region, the controller 320 may control the display 160 to display an ultrasonic image of the object ob.

FIG. 5C illustrates that eyes E of a user are provided in the third region. In FIG. 5C, the third region may represent a region between dotted lines extending from the camera 310.

The camera 310 may generate an image including eyes E of a user, and based on the image, the controller 320 may determine that the eyes E of the user are positioned in the third region. According to the determination, the controller 320 controls the display 160 to display a CT image of the object ob.

As described above, without an additional input to select the type of an image, a user may receive a desired type of an image corresponding to the change in a sightline of the user. In particular, a user performs an ultrasonic diagnosis while grasping the ultrasonic probe 200 with his/her hands, which may cause difficulty in inputting a command to control an ultrasonic apparatus. However, the ultrasonic apparatus according to the exemplary embodiment allows a user to easily switch an image being displayed, without requiring the use of the hands of the user.

Meanwhile, since the camera 310 generates an image which includes the eyes E of a user, the controller 320 also determines the positions of the eyes E of the user in real time. Accordingly, the display 160 may display one of an ultrasonic image, an external image and a composite image of the ultrasonic image and the external image according to a predetermined frame rate.

In this case, the controller 320 may control the display 160 to display an image having the same type as that of an image displayed in a previous frame if the determined position of the eyes E is identical to the previously determined position of the eyes E.

The display 160 may display an image having the same type as that of an image displayed in a n−1$^{th}$ frame if $\theta_{mn}$ formed between a sightline determined in a n$^{th}$ frame and the reference line is equal to $\theta_{mn-1}$ acquired in the n−1$^{th}$ frame. For example, if the display 160 displays an ultrasonic image in the n−1$^{th}$ frame, an ultrasonic image is displayed even in the n$^{th}$ frame.

In this aspect, if the $\theta_{mn}$ is identical to the previously acquired $\theta_{mn-1}$, a user does not need to determine a region to which the sightline of the user belongs. Accordingly, the controller 320 may rapidly control the display 160.

Figure 6:
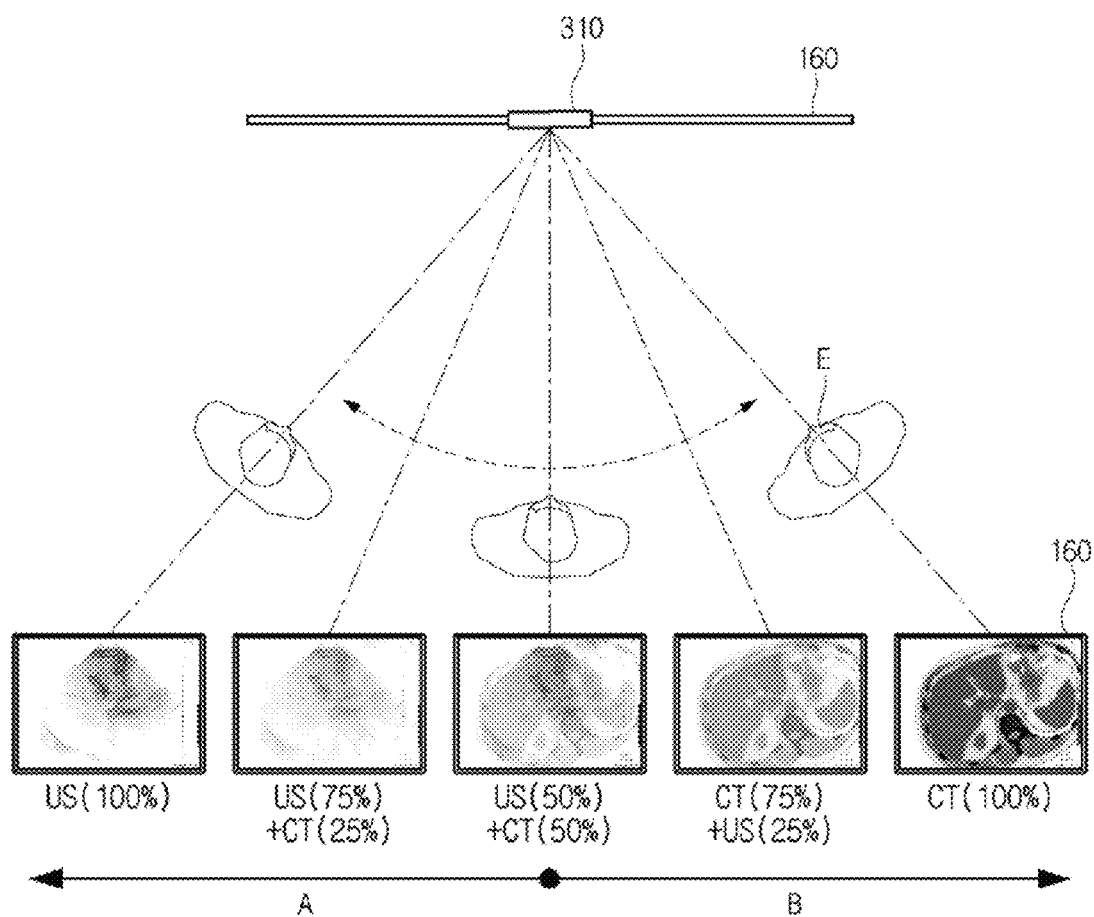
FIG. 6 is a view illustrating a display method of an ultrasonic apparatus, in accordance with another exemplary embodiment.

FIG. 6 is a view illustrating a display method of an ultrasonic apparatus, in accordance with another exemplary embodiment. The description of FIG. 6 will be made on the assumption that the external image is a CT image.

Different from the exemplary embodiment described with reference to FIGS. 5A, 5B, and 5C, the controller 320 may control the display 160 to display a composite image combined in a ratio corresponding to the determined position of eyes E. In detail, the controller 320 may determine a composition ratio based on the difference between the determined position of eyes E and a predetermined reference line, and displays an image based on a combination which uses the determined composition ratio.

The difference between the position of eyes E and the reference line may represent an angle between a sightline, which starts from the position of the eyes E and ends at the center of the lens, and the reference line.

The controller 320, if the position of the eyes E of a user is included in the reference line, controls the display 160 to display a composite image in which is generated by using an equal ratio of the ultrasonic image and the external image for performing the combination.

Referring to FIG. 6, when the sightline of a user is aligned with the reference line, the display is configured to display an image combined with 50% of an ultrasonic image and 50% of a CT image.

In addition, the controller 320 may control the display 160 to display an image combined in a higher proportion of a first one of the ultrasonic image and the external image relative to the other one of the ultrasonic image and the external image as a difference between the sightline of a user and the reference line increases.

Referring to FIG. 6, when the eyes E of a user are moved to the left, the display 160 may display an image combined in a higher proportion of an ultrasonic image relative to a CT image. In particular, when the sightline of a user is coincident with the left side boundary of an angle of view, the display 160 displays 100% of an ultrasonic image.

Meanwhile, when the eyes E of a user are moved to the right, the display 160 may display an image combined in a higher proportion of a CT image relative to an ultrasonic image. In particular, when the sightline of a user is coincident with the right side boundary of an angle of view, the display 160 displays 100% of a CT image.

In particular, when the eyes move in direction A on FIG. 6, a composite image having a higher proportion of an ultrasonic image is displayed, and when the eyes move in direction B, a composite image having a higher proportion of a CT image is displayed.

Alternatively, different from FIG. 6, when the eyes E of a user are moved to the left, the display 160 may display an image combined in a higher proportion of a CT image relative to an ultrasonic image, and when the eyes E of a user are moved to the right, the display 160 may display an image combined in a higher proportion of an ultrasonic image relative to a CT image.

According to the exemplary embodiment described with reference to FIG. 6, when the position of eyes E of a user is continuously varied, the composition ratio of an ultrasonic image and a CT image may be continuously varied. As a result, a user may be selectively provided with composite images which are generated by performing combinations which use various ratios.

In this case, the controller 320, if the determined position of the eyes E is identical to the previously determined position of the eyes E, may control the display 160 to display an image having the same type as that of an image displayed in a previous frame.

The display 160 may display an image having the same type as that of an image displayed in a n−1$^{th}$ frame if $\theta_{mn}$ formed between a user's sightline acquired based on the position of the eyes E determined in a n$^{th}$ frame and the reference line is equal to $\theta_{-1}$ acquired in the n−1$^{th}$ frame. For example, if the display 160 displays a composite image including 75% of an ultrasonic image and 25% of a CT image in the n−1$^{th}$ frame, a composite image including 75% of an ultrasonic image and 25% of a CT image is displayed even in the n$^{th}$ frame.

In particular, if the $\theta_m$ is identical to the previously acquired $\theta_{mn-1}$, the controller 320 may rapidly determine an image to be displayed.

Referring again to FIG. 3A, the display 160 displays one of an ultrasonic image, an external image and a composite image of an ultrasonic image and an external image according to control of the controller 320.

In this case, the display 160 may provide one of the ultrasonic image, the external image and the composite image in 3D such that a user recognizes the images in 3D. In this case, the ultrasonic image may be a 3D image generated based on volume data which relates to an object ob.

To this end, the display 160 may be designed such that a left eye and a right eye of a user recognize different images, respectively. Description thereof has been made above, and thus the details will be omitted.

Meanwhile, different from FIG. 3A, the image processor 170 may receive an external image via the network. FIG. 3B illustrates that an ultrasonic apparatus, a magnetic resonance imaging apparatus M and a computerized tomography apparatus C are connected to the same network.

The ultrasonic apparatus may receive an MR image from the magnetic resonance imaging apparatus M and/or receive a CT image from the computerized tomography apparatus C via the network.

Alternatively, different from FIGS. 3A and 3B, the storage 400 provided in the ultrasonic apparatus may store external images of an object ob in advance. Referring to FIG. 3C, the controller 320 may retrieve an external image stored in the storage 400, and may transmit the external image to the image processor 170. The image processor 170 receives the external image stored in the storage 400, registers the received external image with respect to an ultrasonic image, and generates a composite image.

Figure 7:
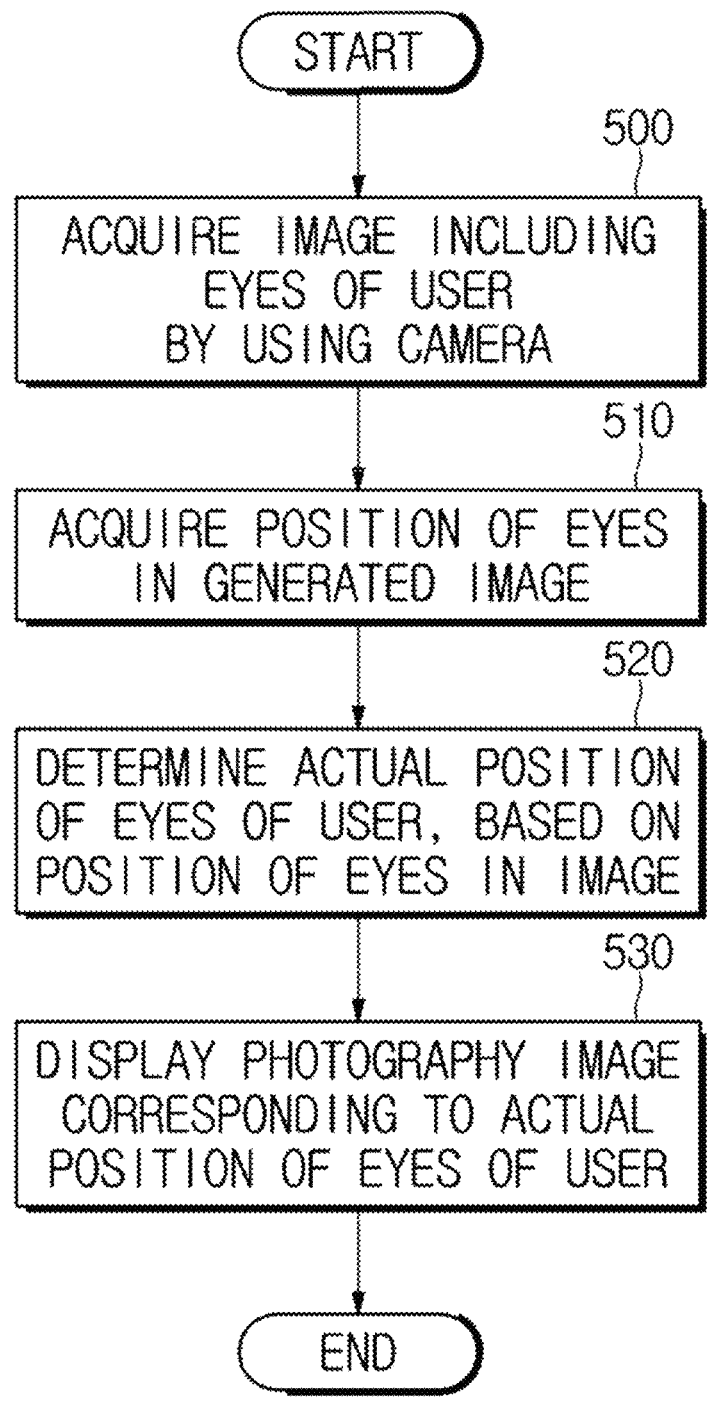
FIG. 7 is a flowchart showing a method of controlling an ultrasonic apparatus, in accordance with an exemplary embodiment.

FIG. 7 is a flowchart showing a method for controlling an ultrasonic apparatus in accordance with an exemplary embodiment. Description of FIG. 7 will be made in relation to a method for recognizing the position of eyes E of a user.

First, in operation 500, an image which includes eyes E of a user is generated by using the camera 310. In this case, the camera 310 may form an optical image of the eyes of the user on an image plane of the image pickup device.

After the image including the eyes E of the user is generated, in operation 510, the position of the eyes E in the generated image is acquired. In this case, the position of the eyes in the generated image is acquired while having a point passed by an optical axis on an image plane as the origin.

After the position of the eyes in the image is acquired, in operation 520, the actual position of the eyes of the user is determined by using the acquired position of the eyes.

Finally, in operation 530, a photography image corresponding to the determined position of the eyes E of the user is displayed. In this case, the photography image may include any of an ultrasonic image, an external image and a composite image of an ultrasonic image and an external image.

Figure 8:
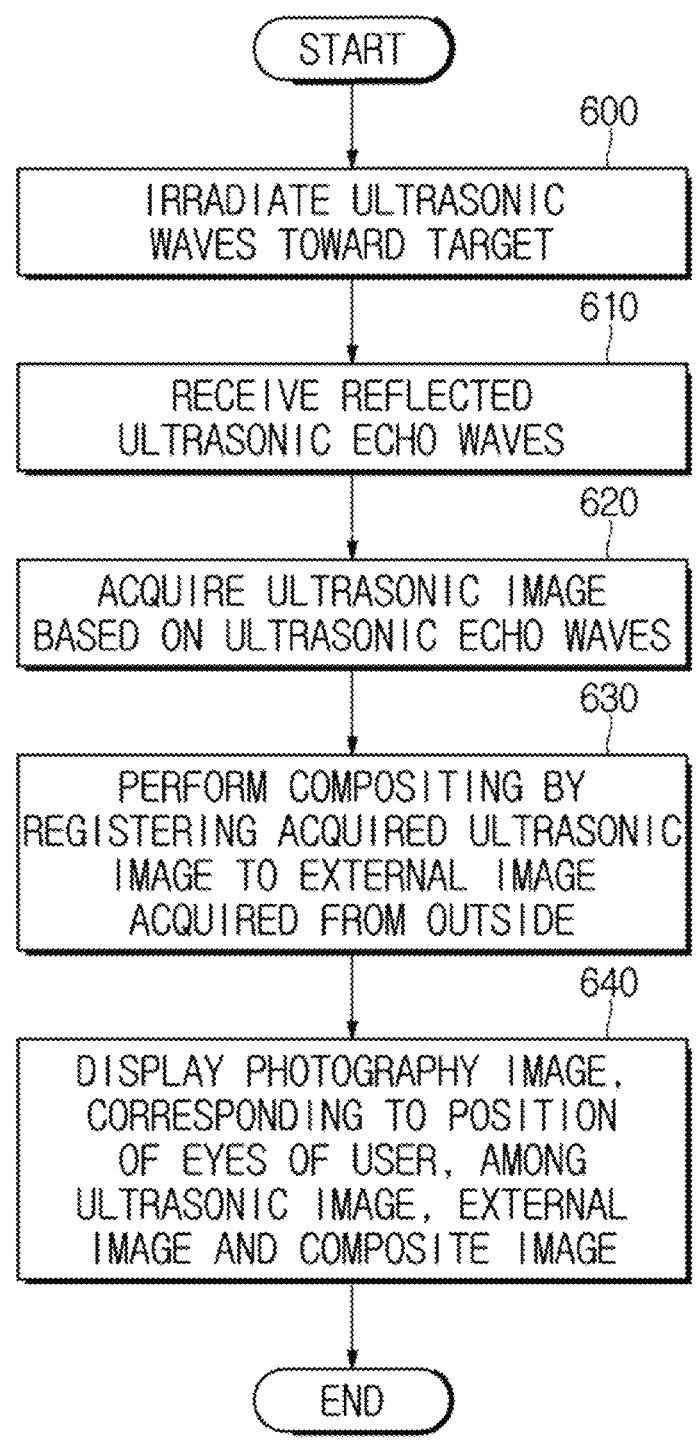
FIG. 8 is a flowchart showing a method of controlling an ultrasonic apparatus, in accordance with another exemplary embodiment.

FIG. 8 is a flowchart showing a method for controlling an ultrasonic apparatus, in accordance with another exemplary embodiment. Description of FIG. 8 will be made in relation to a method for generating a composite image.

First, in operation 600, ultrasonic waves are irradiated toward an object. In response to the irradiation of ultrasonic waves, in operation 610, echo ultrasonic waves reflected from the object ob are received.

Thereafter, in operation 620, an ultrasonic image is acquired based on the received echo ultrasonic waves. If the received echo ultrasonic waves include volume data which relates to an object ob, the ultrasonic image may be a 3D ultrasonic image.

The ultrasonic image acquired as such is registered to an external image acquired from outside in operation 630, thereby effecting a combination of the ultrasonic image and the external image. In this case, the outside may include an external apparatus or an external network, and the external image may represent a photography image of an object ob acquired from the outside.

In order to register the ultrasonic image to the external image, coordinate systems of the two images may be aligned. In addition, by overlaying the two images based on the aligned coordinate systems, a composite image is generated. In this case, the composition ratio may be determined depending on by varying the degrees of opacity of the two images.

Finally, in operation 640, a photography image corresponding to the position of the eyes E of a user from among an ultrasonic image, an external image and a composite image thereof is displayed. In this case, the recognizing of the position of the eyes has been already described above with respect to FIG. 7.

Figure 9:
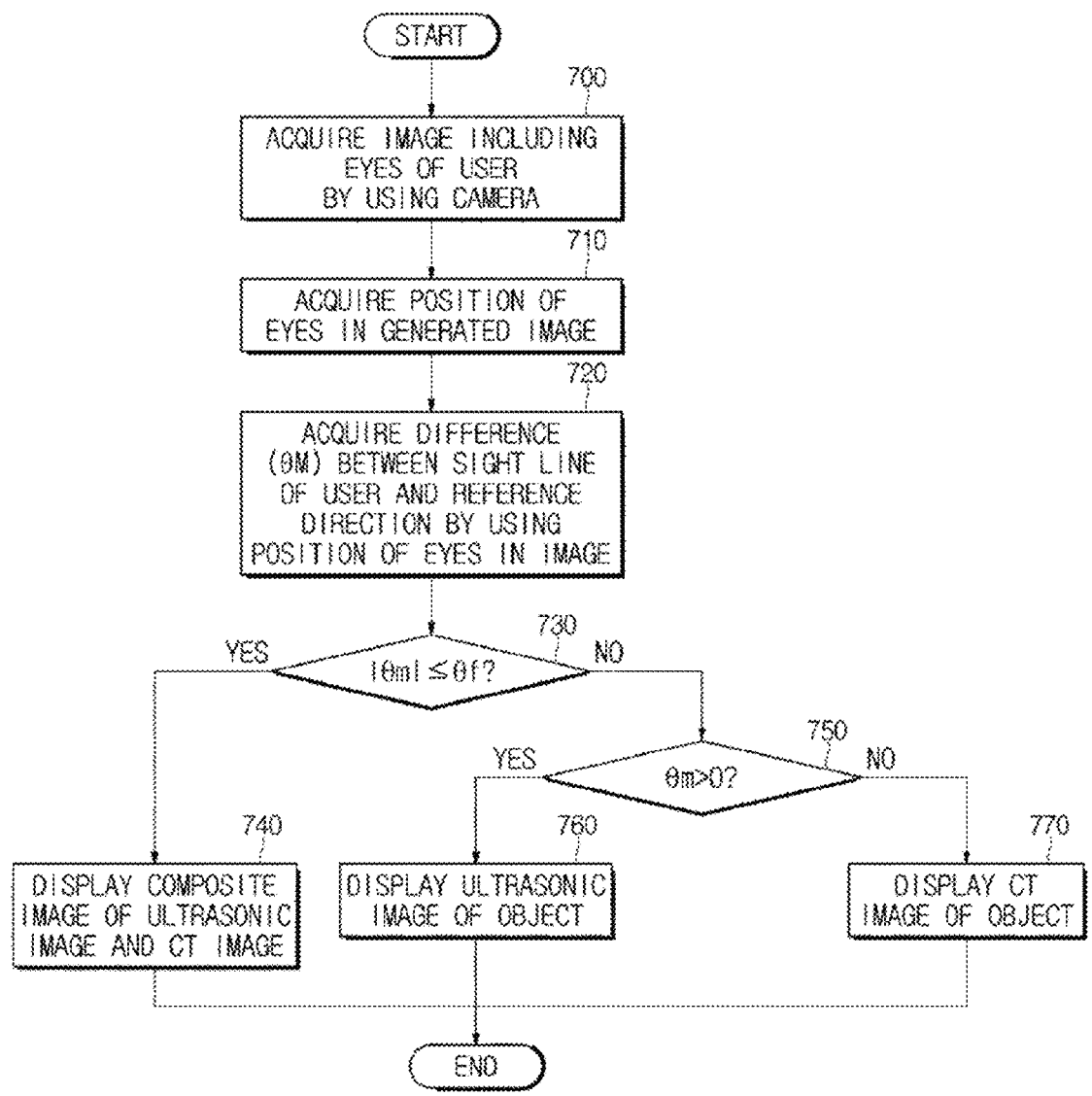
FIG. 9 is a flowchart showing a method of controlling an ultrasonic apparatus, in accordance with still another exemplary embodiment.

FIG. 9 is a flowchart showing a method for controlling an ultrasonic apparatus, in accordance with still another exemplary embodiment.

First, in operation 700, an image which includes eyes E of a user is generated by using the camera 310. In this case, the camera 310 may form an optical image of the eyes of the user on an image plane of the image pickup device.

After the image including the eyes E of the user is generated, in operation 710, the position of the eyes in the generated image is acquired.

After the position of the eyes in the image is acquired, in operation 720, the difference $\theta\theta_m$ between the sightline and the reference direction is acquired by using the position of the eyes. In this case, an angle of view of the camera 310 and the width of the image plane may be used. The method of acquiring $\theta\theta_m$ may be achieved by using Equation 1 and Equation 2 as described above.

Thereafter, in operation 730, it is determined whether an absolute value of $\theta_m$ is equal to or smaller than $\theta_f$. $\theta_f$ may be a positive real number.

If $\theta\theta_m$ belongs to a range of between $-\theta_f$ and $\theta_f$, the position of the eyes is determined to be provided in a region for which a composite image is displayed. Accordingly, when the absolute value of $\theta_m$ is equal to or smaller than $\theta_f$, in operation 740, a composite image of an ultrasonic image and a CT image is displayed.

If the absolute value of $\theta_m$ is larger than $\theta_f$, in operation 750, it is determined that $\theta_m$ is a positive value. If $\theta_m$ is larger than $\theta_f$, the position of eyes is determined to be provided in a region for which an ultrasonic image is displayed. Accordingly, if $\theta_m$ is a positive value, in operation 760, an ultrasonic image of an object ob is displayed.

If $\theta_m$ is smaller than $-\theta_f$, the position of the eyes is determined to be provided in a region for which a CT image is displayed. Accordingly, if $\theta_m$ is a negative value, in operation 770, a CT image of an object ob is displayed.

Figure 10:
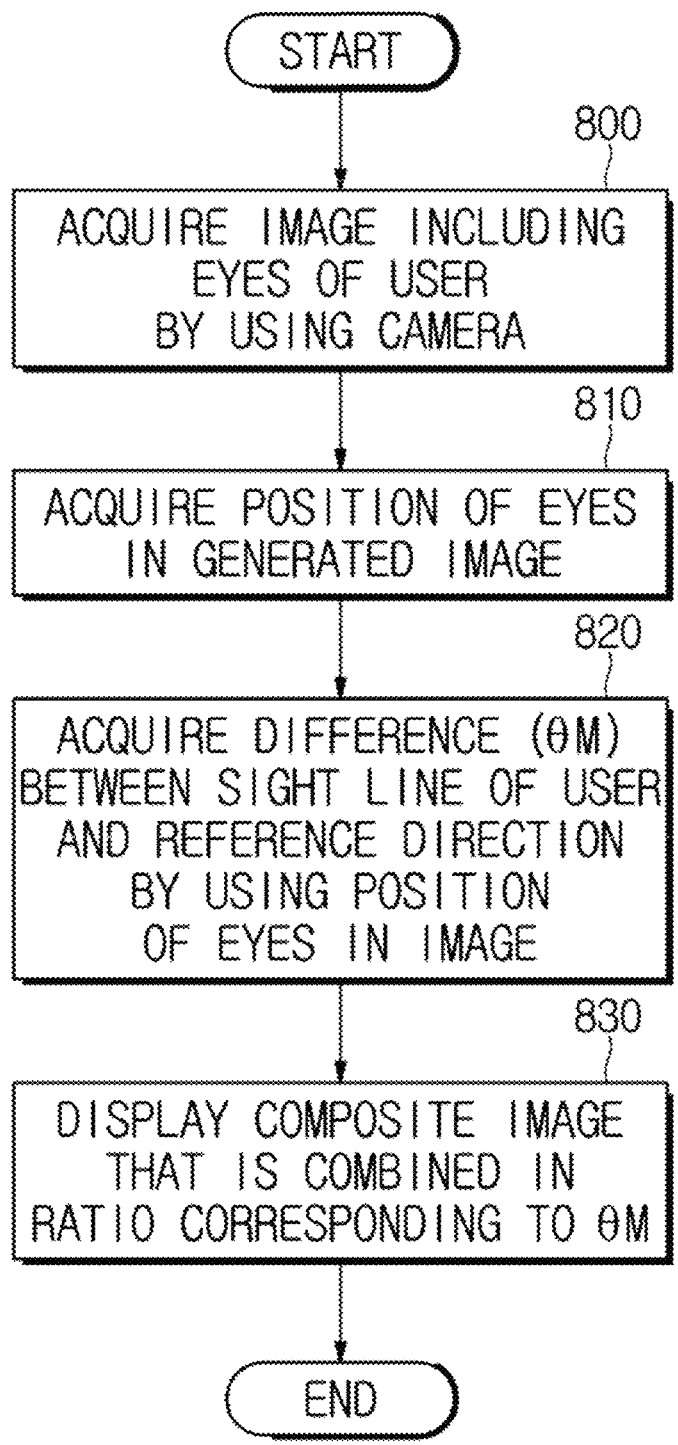
FIG. 10 is a flowchart showing a method of controlling an ultrasonic apparatus, in accordance with still another exemplary embodiment.

FIG. 10 is a flowchart showing a method for controlling an ultrasonic apparatus, in accordance with still another exemplary embodiment.

First, in operation 800, an image which includes eyes E of a user may be generated by using the camera 310. In this case, the camera 310 may form an optical image of the eyes of the user on an image plane of the image pick up device.

After the image including the eyes of the user is generated, in operation 810, the position of the eyes in the generated image is acquired. In this case, the position of the eyes E in the image is determined by the number of pixels of the image plane.

After the position of the eyes in the image is acquired, in operation 820, the difference $\theta_m$ between the sightline of the user and the reference direction is acquired by using the position of the eyes. In this case, the method of acquiring $\theta_m$ may be achieved by using Equation 1 and Equation 2 as described above.

Finally, in operation 830, a composite image combined in a composition ratio corresponding to the acquired $\theta_m$ is displayed. The composite image represents an image generated by combining an ultrasonic image and an external image in a ratio corresponding to $\theta_m$. In addition, the composition ratio may represent respective degrees of opacity of the images.

For example, if $\theta_m$ is equal to zero (0), a composite image combined in an equal ratio of the ultrasonic image and the external image may be displayed. Meanwhile, it is possible to display a composite image combined in a higher proportion of a first one of the ultrasonic image and the external image with respect to the other image if $\theta_m$ becomes increased.

FIG. 11 is a flowchart showing a method for controlling an ultrasonic apparatus, in accordance with still another exemplary embodiment.

In operation 900, an initial value of n, that is, the frame number, is set to be equal to 1.

In operation 910, an image which includes eyes E of a user is generated by using the camera 310. In this case, the camera 310 may form an optical image of the eyes of the user on an image plane of the image pickup device.

After the image including the eyes E of the user is generated, in operation 920, the position of the eyes E in the generated image is acquired. In this case, the position of the eyes in the image is acquired while having a point passed by an optical axis on an image plane as the origin.

After the position of the eyes in the image is acquired, in operation 930, the difference $\theta_m$ between the sightline of the user and the reference direction is acquired by using the position of the eyes. In this case, an angle of view of the camera 310 and the width of the image plane may be used.

Thereafter, in operation 940, a photography image corresponding to $\theta_m$ is displayed. In this case, the photography image may include any of an ultrasonic image, an external image and a composite image of an ultrasonic image and an external image.

Thereafter, in operation 950, it is determined if there is a need to continue displaying a photography image. If it is determined there is no need to continue displaying a photography image, the operation ends.

If it is determined there is a need to keep displaying a photography image, then in operation 960, the frame number n increases by 1. As a result, the above described processes are repeated to display a photography image of a n+1$^{th}$ frame.

FIG. 12 is a flowchart showing a method for controlling an ultrasonic apparatus, in accordance with still another exemplary embodiment.

In operation 1000, an initial value of n, that is, the frame number, is set to be equal to 1 (1000).

In operation 1010, an image which includes eyes E of a user is generated by using the camera 310. After the image including the eyes E of the user is generated, in operation 1020, the position of the eyes E in the generated image is acquired.

After the position of the eyes in the image is acquired, in operation 1030, the difference $\theta_m$ between the sightline of the user and the reference direction is acquired by using the position of the eyes. In this case, an angle of view of the camera 310 and the width of the image plane may be used.

Thereafter, in operation 1040, it is determined whether or not the frame number is equal to 1.

If it is determined that the frame number is equal to or greater than 2, in operation 1050, it is determined whether or not $\theta_{mn}$ is equal to $\theta_{mn-1}$. In this operation, it is determined whether the current position of the eyes of the user is identical to the position of the eyes of the user in the previous frame.

If it is determined that $\theta_{mn}$ is equal to $\theta_{mn-1}$, in operation 1060, an image having the same type as that of an image displayed in the previous frame is displayed. For example, if a composite image including 25% of an ultrasonic image and 75% of an external image is displayed in the previous frame, a composite image having the same ratio as that of the previous frame is displayed even in the current frame.

If it is determined that the frame number is 1 or $\theta_{mn}$ is not equal to $\theta_{mn-1}$, in operation 1070, a photograph image corresponding to $\theta_{mn}$ is displayed.

Thereafter, in operation 1080, it is determined if there is a need to continue displaying a photography image. If it is determined there is no need to continue displaying a photography image, the operation ends.

Meanwhile, if it is determined there is a need to continue displaying a photography image, in operation 1090, the frame number n increases by 1. As a result, the above described processes are repeated to display a photography image of a n+1$^{th}$ frame.

According to the ultrasonic apparatus according to an exemplary embodiment and the control method thereof, an image switch is easily switched without requiring an additional input by recognizing the position of eyes of a user and displaying an image corresponding to the recognition.

According to the ultrasonic apparatus according to another exemplary embodiment and the control method thereof, a user is selectively provided with an image having different types of images combined in a varied composition ratio, thereby providing composite images having various conditions that are selectable by a user.

Although a few exemplary embodiments have been shown and described, it will be appreciated by those of skill in the art that changes may be made in these exemplary embodiments without departing from the principles and spirit of the present inventive concept, the scope of which is defined in the claims and their equivalents.

What is claimed is:
1. An ultrasonic apparatus comprising:
   a storage configured to store an external image of an object;
   an image processor configured to generate a composite image by registering an ultrasonic image of the object with respect to the stored external image;
   a recognizer configured to recognize a position of eyes of a user; and
   a display configured to display one of the ultrasonic image, the external image and the composite image based on the recognized position of the eyes of the user, wherein the display is further configured to display the composite image based on an opacity ratio between the ultrasonic image and the external image, which is used for performing the registering and which corresponds to a sightline of the user which is determined by using the recognized position of the eyes, and wherein the opacity ratio is determined based on a difference between the determined sightline and a predetermined reference line.

2. The ultrasonic apparatus of claim 1, wherein the image processor is further configured to generate the composite image by registering the ultrasonic image with respect to at least one of a computed tomography (CT) image, a magnetic resonance (MR) image and a positron emission tomography (PET) image of the object.

3. The ultrasonic apparatus of claim 1, wherein the display is further configured to display the composite image if the recognized position of the eyes belongs to a predetermined first region, to display the ultrasonic image if the recognized position of the eyes belongs to a predetermined second region, and to display the external image if the recognized position of the eyes belongs to a predetermined third region.

4. The ultrasonic apparatus of claim 1, wherein the ratio corresponds to an equal weighting of the ultrasonic image and the external image if the determined sightline is aligned with the reference line.

5. The ultrasonic apparatus of claim 1, wherein the image processor is further configured to generate the composite image by increasing a relative proportion of one of the ultrasonic image and the external image with respect to the other of the ultrasonic image and the external image as a difference between the determined sightline and the reference line increases.

6. The ultrasonic apparatus of claim 1, wherein the display is further configured to display one of the ultrasonic image, the external image and the composite image in a three dimensional depiction.

7. The ultrasonic apparatus of claim 6, wherein the ultrasonic image is generated based on volume data which relates to the object.

8. The ultrasonic apparatus of claim 1, wherein the recognizer comprises:
   a camera configured to acquire an image which includes the eyes of the user; and
   a controller configured to determine the recognized position of the eyes of the user, based on a respective position of the eyes in the acquired image.

9. The ultrasonic apparatus of claim 8, wherein the recognizer is further configured to recognize the position of the eyes of the user by using at least one from among a horizontal width of an image plane of the camera and an angle of view of the image plane of the camera.

10. The ultrasonic apparatus of claim 1, wherein the display is further configured to display an image having a same type as a type of an image displayed in a previous frame if the recognized position of the eyes is identical to a position of the eyes which has previously been recognized.

11. A method for controlling an ultrasonic apparatus, the method comprising:
   generating a composite image by registering an ultrasonic image of an object with respect to an external image of the object;
   recognizing a position of eyes of a user; and
   displaying one of the ultrasonic image, the external image and the composite image, based on the recognized position of the eyes of the user,
   wherein the displaying comprises displaying the composite image based on an opacity ratio between the ultrasonic image and the external image, which is used for performing the registering and which corresponds to a sightline of the user which is determined by using the recognized position of the eyes, and
   wherein the opacity ratio is determined based on a difference between the determined sightline and a predetermined reference line.

12. The method of claim 11, wherein the generating the composite image comprises registering the ultrasonic image with respect to at least one of a computed tomography (CT) image, a magnetic resonance (MR) image and a positron emission tomograpy (PET) image of the object.

13. The method of claim 11, wherein in the displaying of one of the ultrasonic image, the external image and the composite image,
   the composite image is displayed if the recognized position of the eyes belongs to a predetermined first region, the ultrasonic image is displayed if the recognized position of the eyes belongs to a predetermined second region, and the external image is displayed if the recognized position of the eyes belongs to a predetermined third region.

14. The method of claim 11, wherein the ratio corresponds to an equal weighting of the ultrasonic image and the external image if the determined sightline is aligned with the reference line.

15. The method of claim 11, wherein the generating the composite image comprises increasing a relative proportion of one of the ultrasonic image and the external image with respect to the other of the ultrasonic image and the external image as a difference between the determined sightline and the reference line increases.

16. The method of claim 11, wherein the displaying one of the ultrasonic image, the external image and the composite image comprises displaying one of the ultrasonic image, the external image and the composite image in a three dimensional depiction.

17. The method of claim 16, wherein the ultrasonic image is generated based on volume data which relates to the object.

18. The method of claim 11, wherein the recognizing the position of the eyes of the user comprises:
   acquiring an image which includes the eyes of the user; and
   determining the recognized position of the eyes of the user, based on a respective position of the eyes in the acquired image.

19. The method of claim 18, wherein the recognizing the position of the eyes comprises using at least one from among a horizontal width of an image plane of a camera configured to acquire the image and an angle of view of the image plane of the camera.

20. The method of claim 11, wherein the displaying comprises displaying an image having a same type as a type of an image displayed in a previous frame if the recognized position of the eyes is identical to a position of the eyes has previously been recognized.

* * * * *